United States Patent
Zhou et al.

(10) Patent No.: US 6,534,661 B1
(45) Date of Patent: Mar. 18, 2003

(54) INTEGRATED PROCESS AND DUAL-FUNCTION CATALYST FOR OLEFIN EPOXIDATION

(75) Inventors: Bing Zhou, Cranbury, NJ (US); Michael Rueter, Plymouth Meeting, PA (US)

(73) Assignee: Hydrocarbon Technologies, Inc., Lawrenceville, NJ (US)

( * ) Notice: Subject to any disclaimer, the term of this patent is extended or adjusted under 35 U.S.C. 154(b) by 0 days.

(21) Appl. No.: 09/996,920

(22) Filed: Nov. 30, 2001

Related U.S. Application Data

(60) Provisional application No. 60/258,535, filed on Dec. 28, 2000.

(51) Int. Cl.[7] .................. B01J 29/89; B01J 29/068; C01B 15/029; C07D 301/12; C07D 301/03
(52) U.S. Cl. .................. 549/531; 549/532; 549/524; 423/584; 502/64; 502/66; 502/71; 502/74; 502/77
(58) Field of Search .................. 502/64, 66, 71, 502/74, 77; 423/584; 549/531, 532, 524

(56) References Cited

U.S. PATENT DOCUMENTS

| | | | |
|---|---|---|---|
| 6,090,858 A | | 7/2000 | El-Sayed |
| 6,106,797 A | * | 8/2000 | Muller et al. ............... 423/584 |
| 6,168,775 B1 | | 1/2001 | Zhou |
| 6,284,213 B1 | | 9/2001 | Paparatto |
| 6,307,073 B1 | * | 10/2001 | Jones .......................... 549/532 |
| 2002/0025293 A1 | | 2/2002 | Paparatto et al. |

FOREIGN PATENT DOCUMENTS

| | | |
|---|---|---|
| EP | 0864362 A1 | 9/1998 |
| EP | 1160196 A1 | 12/2001 |

\* cited by examiner

*Primary Examiner*—Tom Dunn
*Assistant Examiner*—Christina Ildebrando
(74) *Attorney, Agent, or Firm*—Daniel M. Kennedy

(57) ABSTRACT

The invention discloses a dual-functional catalyst composition and an integrated process for production of olefin epoxides including propylene oxide by catalytic reaction of hydrogen peroxide from hydrogen and oxygen with olefin feeds such as propylene. The epoxides and hydrogen peroxide are preferably produced simultaneously in situ. The dual-functional catalyst comprises noble metal crystallites with dimensions on the nanometer scale (on the order of <1 nm to 10 nm), specially dispersed on titanium silicalite substrate particles. The dual functional catalyst catalyzes both the direct reaction of hydrogen and oxygen to generate hydrogen peroxide intermediate on the noble metal catalyst surface and the reaction of the hydrogen peroxide intermediate with the propylene feed to generate propylene oxide product. Combining both these functions in a single catalyst provides a very efficient integrated process operable below the flammability limits of hydrogen and highly selective for the production of hydrogen peroxide to produce olefin oxides such as propylene oxide without formation of undesired co-products.

37 Claims, 2 Drawing Sheets

(HT-18)

a. (110)　　　　　b. (100)　　　　　c. (111)

SURFACE STRUCTURE OF DIFFERENT Pd CRYSTAL PHASES

FIRST LAYER　　SECOND LAYER　　THIRD LAYER (HT-18)

INTEGRATED PROCESS AND DUAL-FUNCTION CATALYST FOR OLEFIN EPOXIDATION

CROSS-REFERENCE TO RELATED APPLICATIONS

This application claims the benefits of related U.S. Provisional Patent Application serial No. 60/258,535, filed Dec. 28, 2000.

This invention was made with support under Contract No. DE-FG02-01ER83350 awarded by the Department of Energy, and the Government has certain rights in this invention.

FIELD OF THE INVENTION

This invention provides an integrated process using a dual-functional catalyst for producing epoxides of olefins. In particular, it relates to the production of propylene oxide from propylene wherein the hydrogen peroxide intermediate oxidizing or epoxidizing agent is produced in-situ for the concomitant epoxidation of propylene.

BACKGROUND OF INVENTION

Improved methods of producing propylene oxide or epoxide (PO) have long been sought. The current conventional technologies for PO production are based on the catalytic epoxidation of propylene using organic hydroperoxides such as tertiary-butyl hydroperoxide (TBHP) or ethyl benzene hydroperoxide (EBHP). The TBHP and EBHP are generated by the non-catalytic autooxidation of organic substrates (isobutane or ethyl benzene) with oxygen. However, these existing processes have important drawbacks, which involve multiple reaction steps with intervening distillation separations, resulting in high equipment counts and high capital investment costs. The hydrocarbon substrate feed is first oxidized in a first reactor to generate the hydroperoxide intermediate, which is generally then distilled to recover a portion of the unreacted feed and increase the concentration of the hydroperoxide. The concentrated hydroperoxide is then contacted with propylene feed in a second reactor over a suitable catalyst to generate propylene oxide. A series of separation steps must then be conducted, typically by distillation, to recover the propylene oxide product in purified form.

The complexity of the current process is increased by the fact that for every molecule of propylene oxide primary product generated, at least one molecule of a secondary product is generated. In the case of TBHP intermediate, the secondary product is tertiary-butyl alcohol (TBA), while the use of EBHP leads to the formation of acetophenone. In and of themselves these products are not typically desirable as they require further processing with at least two additional reactors and further distillation to generate more desirable products. TBA is generally converted to methyl tertiary-butyl ether (MTBE) in a two-stage process, first by dehydration to form isobutylene, and then reaction with methanol to form MTBE. Acetophenone is first hydrogenated to form methyl benzyl alcohol, which is then dehydrated to form styrene. These additional steps add undesirable capital and operating costs to the conventional propylene oxide process.

In addition to the added cost and complexity, the production of these secondary products adds further difficulty, because on a weight basis these secondary products are produced in greater amount than the desired propylene oxide product. Commercial markets must be found for the secondary products, and the profitability of the propylene oxide plant is highly influenced by the profitability of the markets for MTBE and styrene. The MTBE market, dominated by use in reformulated gasoline, is currently under severe strain because of environmental and health concerns related to its use. The styrene market is highly cyclical, and is too large to be effectively influenced by propylene oxide producers who produce styrene only as a by-product. As a consequence of these various problems with existing propylene oxide processes, considerable research has been directed towards developing alternate processes for propylene oxide production. Generally, this work has sought to develop processes that eliminate the formation of any secondary product along with the desirable propylene oxide.

Another category of propylene oxide processes is based on direct oxidation of propylene with oxygen. For example, U.S. Pat. Nos. 5,698,719; 5,686,380, 5,864,047; 5,625,084; 5,861,519; and 5,763,630 disclose catalysts based on silver for the direct oxidation of propylene to propylene oxide. U.S. Pat. No. 5,703,254 discloses combining silver and gold as catalyst. U.S. Pat. No. 5,760,254 discloses a nitrogen oxide catalyst. U.S. Pat. No. 5,670,674 discloses a platinum-based catalyst. However, none of these patented processes have yet reached a status suitable for commercialization. Generally, the overoxidation of propylene to form carbon oxides such as $CO_2$ is a major problem. A suitable combination of catalyst activity, selectivity, and catalyst life has yet to be achieved, and is likely to present a continuing challenge due to the tendency of molecular oxygen to cause complete oxidation reactions to form $CO_2$.

An alternate approach to a new propylene oxide process is the use of hydrogen peroxide as the oxidizing agent. Unlike organic hydroperoxides such as TBHP and EBHP that form organic by-products during the epoxidation of propylene, the by-product of reacting propylene with hydrogen peroxide is water, an innocuous compound. U.S. Pat. No. 4,701,428 discloses a titanium silicalite catalyst (TS-1), which can be used for the epoxidation of olefins using hydrogen peroxide; this patent is incorporated herein by reference with respect to the titanium silicalite portion of the disclosure. In the epoxidation of propylene to form propylene oxide, selectivity as high as 93% is obtained, based on hydrogen peroxide consumed. Other similar patents are U.S. Pat. Nos. 4,859,785 and 4,954,653. U.S. Pat. Nos. 4,937,216 and 4,824,976 also disclose processes based on TS-1 catalyst for the epoxidation of various olefins, including propylene, and they report selectivities of epoxide formation as high as 98%.

U.S. Pat. Nos. 5,166,372; 5,214,168; 5,262,550; 5,384,418; 5,646,314; 5,693,834; 5,523,426; 5,912,367; 6,066,750 all disclose various versions of an olefin epoxidation process (especially a propylene epoxidation process) where a titanium silicalite is used as the epoxidation catalyst and hydrogen peroxide is used as the epoxidizing agent. Generally, in these patents, hydrogen peroxide is generated in a separate reactor by the autooxidation of a secondary alcohol such as isopropanol. U.S. Pat. Nos. 5,679,749; 6,042,807; and 5,977,009 disclose variations on titanium-based zeolitic catalysts containing other components such as tellurium, boron, germanium, niobium, which are claimed to increase the activity or selectivity of the catalyst for the epoxidation of olefins such as propylene. Also, U.S. Pat. Nos. 5,374,747; 5,412,122; 5,527,520; 5,554,356; 5,621,122; 5,684,170; and 5,695,736 disclose catalysts containing Si and Ti which are isomorphous in structure with the zeolite beta structure. These catalysts are claimed to be useful for the selective epoxidation of olefins such as propylene using hydrogen peroxide as an oxidant.

However, there are significant shortcomings for these prior art processes in the hydrogen peroxide-based epoxidation of propylene that have prevented their commercialization. The cost of hydrogen peroxide produced by current means is generally too high for the peroxide-based route to PO product to be economical. Also, these prior art processes are based on a multi-step approach in which hydrogen peroxide is separately generated using suitable oxidation technology, and then the hydrogen peroxide is used to epoxidize propylene. Normally, there are separation steps provided between these reaction steps. Also, the synthesis of hydrogen peroxide by conventional means normally involves the hydrogenation of a working medium such as anthraquinone or secondary alcohol; this must be oxidized in a third reaction step to regenerate the working medium for re-use in the hydrogen peroxide synthesis.

Another approach is to combine the synthesis of hydrogen peroxide and the epoxidation of propylene into a single step reaction. This requires a dual-functional catalyst, capable of catalyzing the direct reaction of hydrogen and oxygen to form hydrogen peroxide, and simultaneously catalyzing the reaction of said hydrogen peroxide with propylene to form propylene oxide product. Examples are provided by U.S. Pat. Nos. 5,973,171; 6,005,123; 6,008,388; and 6,063,942, all of which disclose catalysts based on combinations of titanium or vanadium based zeolitic structures with noble metals such as palladium. The noble metal constituent provides for the catalytic synthesis of in situ or surface hydrogen peroxide, and the titanium or vanadium-based zeolite catalyzes the epoxidation of propylene by the hydrogen peroxide. However, these prior art processes have also fallen short of requirements for commercialization. The prior art dual-functional catalysts is are not sufficiently selective, and the noble metal constituent is generally not bound strongly enough to the substrate surface to prevent loss of metal surface area through metal leaching to the liquid phase or through sintering of metal particles. Because of the high cost of noble metals such as palladium, this loss of active surface area is unacceptable.

These prior art processes have also failed to utilize the role of crystal-face exposition of the noble metal particles in achieving high selectivity of hydrogen peroxide production as taught in applicants' U.S. Pat. No. 6,168,775 B1. The selectivity of the hydrogen peroxide catalyst is highly dependent on the crystal face with the 110 and 220 crystal faces being much preferred for selective synthesis of hydrogen peroxide intermediate from hydrogen and oxygen. U.S. Pat. Nos. 4,661,337; 4,681,751; 4,772,458; 4,832,938; 5,236,692; 5,378,450; 5,399,334; and 5,338,531 disclose various catalysts based on the use of noble metals such as palladium and other platinum group metals for direct synthesis of hydrogen peroxide from hydrogen and oxygen. But by failing to properly control the noble metal crystal face exposition, these prior art catalysts generally have selectivities of hydrogen peroxide synthesis based on hydrogen consumed of less than 85%. Because hydrogen is a costly feedstock, this low selectivity leads to costly inefficiency in the process.

In applicant' U.S. Pat. No. 6,168,775 B1, incorporated herein by reference in its entirety, these problems are addressed for the direct synthesis of hydrogen peroxide from hydrogen and oxygen feeds. In applicant' patent '775, an ionic polymer such as sodium polyacrylate is used during the deposition of active noble metal, such as palladium, onto the support or substrate to form a peroxide synthesis catalyst. The function of the ionic polymer is to act as a dispersing and control agent to disperse the metal particles on the surface and control their face exposition. Accordingly, under the conditions taught in the '775 patent, the desired crystal face of the noble metal particles are selectively exposed. The process of the '775 patent provides a catalyst with very high selectivity of up to 100% for the direct synthesis of hydrogen peroxide from hydrogen and oxygen feeds. In addition, this catalyst is highly active, giving yields of hydrogen peroxide per weight of noble metal per hour greater than known prior art catalysts, despite being operated at hydrogen feed concentrations of less than the hydrogen flammability limit of 4.5 volume percent in oxygen or 4 volume percent in air.

SUMMARY OF INVENTION

An object of this invention is to address the foregoing problems of propylene oxide production by propylene epoxidation by providing an integrated or combined process using a unique porous dual-functional catalyst having high activity, stable structure, and long life. The dual-functional catalyst can both selectively catalyze the formation of hydrogen peroxide from hydrogen and oxygen and epoxidize propylene feeds to form propylene oxide product. Preferably, the process is carried out in situ in the same reaction vessel. This objective is accomplished using a dual-functional catalyst consisting of dispersed noble metal nanometer-sized crystallite particles such as palladium (Pd) on a titanium-based zeolitic catalyst substrate. The noble metal particles are deposited using a colloid solution in which an ionic polymer is used for dispersing the particles, thereby creating a high surface area of active noble metal having a controlled face exposition. The desired dispersion and controlled crystal-face exposition is achieved using a critical molar ratio of noble metal to ionic polymer in the broad range of 1:0.1 to 1:10, depending on the molecular weight of the polymer, with a preferred range of 1:0.5 to 1:5. By controlling the crystal face exposition, the selectivity of the catalyst is maximized. This dual-functional catalyst converts the feed streams of hydrogen, oxygen, and propylene into propylene oxide in single reactor, and operates effectively at hydrogen feed concentrations below the lower flammability limit of 4.5%. The only by-product of this reaction is water, which can be easily separated from the propylene oxide product.

The titanium-based zeolitic substrate is chosen based on its capability to catalyze the hydrogen peroxide-based epoxidation of propylene to form propylene oxide. For example, titanium silicalite (TS-1) is a suitable substrate, but other suitable substrates may also be selected as known to those skilled in this art. Any material which is a solid under process operating conditions and can catalyze the epoxidation of propylene to propylene oxide can be used as a catalytic substrate for the dual-functional catalyst of the invention. Useful noble metals for the dual-function catalyst utilized in this invention are palladium, platinum, gold, iridium, osmium, rhodium, ruthenium, and combinations thereof. The useful broad percentage concentration for the noble metal in the catalyst is 0.01 to 10 wt %, with a preferred range of 0.1–5 wt %. Suitable ionic polymers or other complexing-dispersing polymers for making the noble metal crystallite catalyst should be either negatively charged or have a lone pair of electrons that can attract the positively charged metal ions such as Pd2+. Ionic polymers preferably have molecular weights within the range of about 300–8000, and more preferably 600–6000. Examples of suitable polymers include polyacrylates, polyvinylbenzoates, polyvinyl sulfate, polyvinyl sulfonates, polybiphenyl carbonates, polybenzimidozoles, polypyridines, and other polymer agents having similar molecular structures and properties.

In the hydrogen peroxide production and propylene epoxidation process of the invention the dual functional catalyst is prepared in a solvent by depositing noble metal on a suitable substrate in the presence of a dispersing agent. Preferred solvents include water and lower alcohols such as methanol.

The dual-function catalyst of this invention is employed in an integrated process including a suitable reactor containing the catalyst, along with suitable systems for catalyst recovery and recycle, unreacted feedstock recovery and recycle, and product recovery and purification. Hydrogen, oxygen, and propylene are simultaneously and continuously fed into the reactor. This reactor will preferably be a single reactor chamber or vessel, but may also consist of multiple reactors connected in series or parallel. The reactor(s) is operated at a temperature in the range 0–150° C. and a pressure in the range 100–3000 psig, preferably 10–100° C. and 500–2000 psig. The catalytic reactor may be a fixed bed, slurry, fluidized bed, or other suitable type for contacting the solid catalyst with liquid and gaseous reactants.

The advantages of the invention for the production of propylene oxide product by an integrated process are:(1) a high overall selectivity of propylene oxide formation, greater than 90% with respect to hydrogen feed consumed, and greater than 90% with respect to propylene feed consumed; (2) greatly reduced capital cost because of reduction in major equipment resulting from the single reaction step and the reduced number of separations required to prepare the hydrogen peroxide intermediate; (3) formation of only water as a by-product; (4) safe operation resulting from the hydrogen concentration being maintained below the flammability limit; (5) safe operation owing to the in situ reaction of the peroxide intermediate, eliminating any need to isolate, purify, or otherwise handle peroxide compounds outside of the reactor; and (6) long catalyst life and low loss of active noble metal surface area due to the strong bonding of noble metal particles to the catalyst substrate surface. Because of these advantages, the invention represents a major advance compared to the known prior art processes for propylene oxide production.

In general, the invention comprises a porous particulate dual-functional catalyst for the selective combined in-situ production of hydrogen peroxide from hydrogen and oxygen concurrent with the epoxidation of olefins. The dual-functional catalyst comprises a catalytic substrate material comprising at least one olefin epoxidation catalyst; and at least one crystalline noble metal exhibiting crystallites of nanometer size deposited on a portion of the surface of said substrate. Of particular significance is the fact that the crystallite faces of the deposited noble metal crystals are mainly composed of the 110 and/or 220 series of crystal planes.

Further, the invention includes a method for preparing a porous, dual-functional catalyst comprising nanometer-sized noble metal-containing catalyst crystals deposited on a particulate catalytic substrate for the combined in-situ production of hydrogen peroxide from hydrogen and oxygen concurrent with the epoxidation of an olefins feedstream. The method includes preparing a dilute acid solution containing a noble metal salt including a palladium salt alone or in combination with a minor amount of one or more salts of platinum, gold, iridium, osmium, rhodium or ruthenium; mixing a water-soluble catalyst impregnation control ionic polymer into the dilute acid solution of noble metal salt; reducing the mixed solution of noble metal salt and the impregnation control ionic polymer; adding the particulate catalytic substrate to the reduced mixed solution and impregnating the substrate with the noble metal portion of the reduced mixed solution; recovering and drying the impregnated substrate; and reducing the impregnated substrate with hydrogen to produce the dual-functional catalyst wherein the face of the deposited noble metal crystals are composed mainly of the 110 and/or 220 series of crystal planes.

In addition, a method is disclosed for the epoxidation of olefins simultaneously with the selective in situ generation of hydrogen peroxide. The method comprises concurrently contacting feedstreams comprising hydrogen, oxygen and olefins in a solvent in a reactor vessel containing the particulate dual-functional catalyst described above under reaction conditions sufficient to generate hydrogen peroxide in situ from the hydrogen and oxygen feedstreams while epoxidizing the olefin feedsteam with the in situ generated hydrogen peroxide. A reactor effluent stream is produced containing unreacted gaseous components, particulate catalyst, unconverted liquid olefins, olefin epoxides, solvent and water. The effluent stream is separated to recover the olefin epoxide product and recycle the particulate catalyst, unreacted olefin, unreacted hydrogen, unreacted oxygen and solvent.

While the preferred use of the dual-functional catalyst of the invention is in a process where the hydrogen peroxide production and olefin epoxidation production takes place concurrently, preferably in the same reactor vessel, the process can be carried out sequentially in separate vessels without departing from the scope of the invention. A sequential process of the invention will still enjoy the high selectivity of hydrogen peroxide production at very low hydrogen flammability concentrations but will incur greater vessel counts and similar economic penalties. Thus, a sequential process defeats some of the key advantages inherent in the use of the dual-functional catalyst of the invention for hydrogen peroxide production and olefin epoxidation. The preferred mode of the process of the invention is concurrent in situ production of the aforenoted products.

DETAILED DESCRIPTION OF INVENTION

To solve the aforementioned problems associated with existing commercial and prior art technology for the production of propylene oxide, the present invention provides an integrated process and a new dual-functional combined catalyst for the production of propylene oxide in a single reaction step, using hydrogen, oxygen, and propylene as the reactants, and producing propylene oxide and water as the major product and by-product, respectively. This process and combined catalyst allows propylene oxide to be produced more efficiently, at lower cost, and more safely than has been possible previously. A distinctive and advantageous feature of this invention is the use of a specially prepared dual-functional catalyst, consisting of very fine, nanometer-sized dispersed noble metal catalyst crystallites bound to a substrate of zeolitic catalyst particles. This dual-functional catalyst directly converts a mixture of hydrogen, oxygen, and propylene feeds to propylene oxide product.

A further distinctive and advantageous feature of this invention is the method of preparing the dual functional catalyst particles containing the detailed structure and properties of the noble metal crystals deposited on the particles. The dual functionality of the catalyst is expressed by the hydrogen and oxygen feeds adsorbing and reacting on active sites of the noble metal crystals to form hydrogen peroxide concurrent with the epoxidation of an olefin feedstream by the produced hydrogen peroxide reacting in combination with the catalytic substrate. The hydrogen peroxide is referred to as in-situ hydrogen peroxide, or intermediate hydrogen peroxide. The hydrogen peroxide prepared in the vicinity of noble metal crystal surface of the dual catalyst is in a favorable location to oxidize olefins such as propylene in the vicinity of the titanium-zeolite catalytic substrate portion of the dual catalyst. For the purpose of this invention, the hydrogen peroxide intermediate serves only as the appropriate epoxidizing agent for the subsequent reaction with the olefin feed to form the olefin epoxide. It is not the purpose of this invention to create a net production of hydrogen peroxide; in fact, production of excess hydrogen peroxide is undesirable as it would tend to react with propylene oxide, degrading the desired product, forming undesired by-products, and lowering the overall process selectivity.

Figure 1:
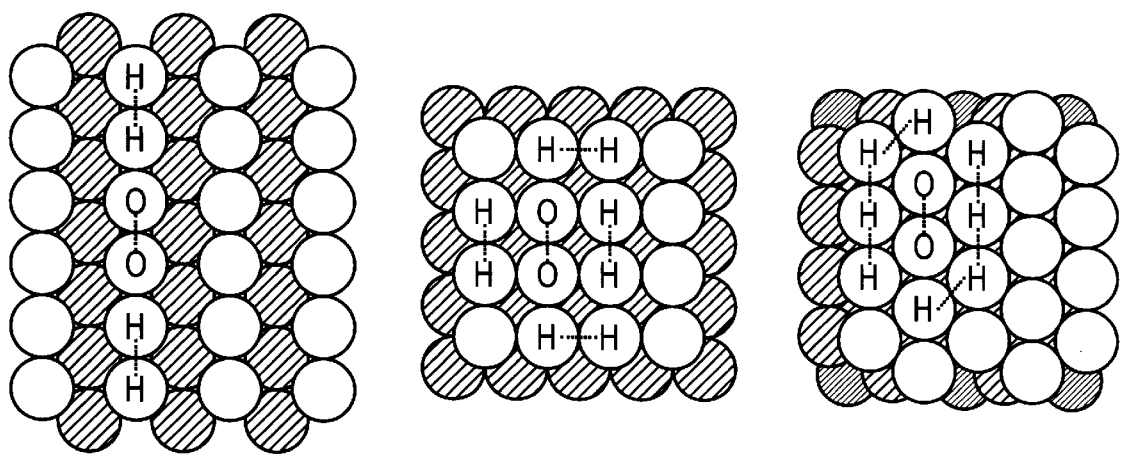
FIGS. 1a–c is a comparative schematic representation of various crystal structures for noble metals such as Pd particles in the catalyst useful for direct production of hydrogen peroxide intermediate, as depicted in U.S. Pat. No. 6,168,775 B1 to applicants.
Figure 1:
Figure 1:
Figure 1:

To achieve a very high selectivity for the generation of in-situ hydrogen peroxide, the dual functional catalyst of the invention must have a precisely controlled structure. The active noble metal constituent of the catalyst plays two important roles, (1) adsorbing oxygen and hydrogen atoms on its surface and (2) aiding electron transfer between the adsorbed oxygen and hydrogen atoms. By adsorbing the oxygen and hydrogen atoms onto the 110/220 crystals planes of the noble metal crystallites, the reactants are activated and brought into a proximity sufficient to promote intermolecular/atomic reactions. By enhancing electron transfer, the rate of intermolecular reactions is increased, leading to the desired catalytic effect. However, electron transfer can occur in a variety of fashions depending upon how many hydrogen and oxygen molecules are adsorbed, and the relative positions and proximity of these molecules to one another. It is for this reason that the crystalline structure of the noble metal particles is critical. FIG. 1 illustrates several possible crystal phase or face expositions of a noble metal particle such as palladium. FIG. 1a depicts a 110 crystal face exposition on which hydrogen and oxygen molecules will be adsorbed in alignment with the linear structure of the top layer of noble metal atoms. As a consequence, each adsorbed oxygen atom can have only one hydrogen atom adsorbed closely enough for electron transfer, which situation favors hydrogen peroxide formation.

FIGS. 1b and 1c show the configurations of the 100 and 111 faces of the noble metal crystals. In these face expositions, an adsorbed oxygen atom can have several nearest hydrogen atoms. By allowing electron transfer with multiple hydrogen atoms, these crystal faces favor the reaction of oxygen with two atoms of hydrogen, leading to the formation of one molecule of water instead of hydrogen peroxide as is desired.

Therefore, in order to provide a dual function catalyst that has a high selectivity for the formation of in situ hydrogen peroxide, its noble metal crystallite portion on the surface of the catalytic substrate should primarily expose the 110 family of crystal faces. (110, 220, etc.). It is one of-the critical aspects of this invention to provide a method for making the catalyst so as to achieve this requirement. This is done by depositing the noble metal particles from a colloid precursor solution, using an ionic polymer as a control agent. The controlling precursor solution is prepared to contain a dissolved noble metal salt and an ionic water-soluble or optionally methanol soluble control polymer in an acidic aqueous medium. The noble metal salt may be a salt of palladium, platinum, gold, iridium, osmium, rhodium, ruthenium, and the like, and combinations thereof, with palladium being preferred. The salt may be any suitable salt of the desired noble metal. In terms of suitability and commercial availability, the preferred choices are chloride and nitrate salts, or combinations thereof. In addition to the primary noble metal salt, such as palladium chloride, a minor amount of a second noble metal salt such as chloroplatinic acid is also included in the precursor solution. This second noble metal salt is useful as an alloying agent; this reduces the solubility of the metal alloy in the precursor solution and prevents the active noble metal from being leached out of the support. This second noble metal salt is added such that the molar ratio of first noble metal to the second noble metal is in the range 20:1 to 100:1.

An ionic polymer is added to the precursor solution, and acts as a control agent. Suitable ionic polymers are either negatively charged or have a lone pair of electrons that can attract the positively charged metal ions such as $Pd^{2+}$. Suitable polymers have molecular weights within the range of about 300–8000, preferably 600–6000. Suitable polymers are water soluble. Examples of suitable polymers include polyacrylates such as polyacrylic acid, polyvinylbenzoates, polyvinyl sulfate, polyvinyl sulfonates, polybiphenyl carbonates, polybenzimidozoles, polypyridines, and other polyacids and polymer agents having similar molecular structures and properties. Sodium polyacrylate is an example of a suitable ionic control polymer. The ionic control polymer is added to the precursor solution such that the molar ratio of noble metal to polymer is in the range 1:0.1 to 1:10, and preferably 1:0.5 to 1:5. This ratio is particularly important, as it greatly affects the catalyst activity. The ratio can be adjusted within the specified range to produce a catalyst with optimal activity.

The desired zeolitic catalyst substrate is mixed into the precursor solution. This zeolitic substrate may be any of a variety of catalytic zeolites that are known to be suitable for the selective epoxidation of olefins, such as the epoxidation of propylene to propylene oxide. These substrates include, but are not limited to, titanium-substituted silicalites such as TS-1, vanadium-substituted silicalites, and titanium-based zeolites containing other components such as tellurium, boron, germanium, and niobium. Appropriate choices will be known and can be identified by those versed in the art. Advantageously, the substrate zeolite should have a surface area of at least about 20 m2/g and usually not exceeding about 1,500 m2/g. The zeolite substrate may be used in a variety of physical forms, depending upon the desired form of the final dual-functional catalyst; for example, it may be a powder of particle size in the range of 1–1000 microns, or it may consist of larger particles, extrudates, tablets, or the like, as would be used in fixed bed reactor applications. If a powdered substrate is used, the resulting catalyst powder will be suitable for use in slurry, fluidized bed, and other related types of reactors. The catalytic substrate may also be further processed by pressing, extrusion, or other appropriate means to generate a catalyst suitable for fixed bed reactors.

By mixing the zeolitic substrate with the precursor solution consisting of noble metal salt and ionic control polymer, the substrate becomes impregnated with the precursor solution. The combination is then dried and reduced under hydrogen atmosphere at a temperature of 100–500° C. and preferably 250–350° C. The resulting dual catalyst has the desired finely dispersed noble metal crystals on the catalytic substrate with the 110 and/or 220 crystal faces preferentially exposed. The final catalyst will have a noble metal loading in the range 0.01 to 10 wt %, preferably 0.1 to 5 wt %. The noble metal crystals or particles on the substrate surface have individual particle or crystallite sizes of 0.1 to 1000 nanometers (nm), preferably 1 to 100 nm.

EXAMPLE 1

Preparation of the Dual-functional Catalyst

Without restricting the scope of this invention, the following provides an illustrative example of a suitable catalyst preparation method or procedure. Palladium chloride is dissolved in a 0.4 wt % hydrochloric acid aqueous solution to form a first solution. A second solution, consisting of sodium polyacrylate in aqueous solution, is added to the first solution, providing a metal to ionic polymer molar ratio in the preferred range of 1:0.5 to 1:5. A third solution of chloroplatinic acid is added to the combined first and second solution to provide a palladium to platinum molar ratio of 20:1 to 100:1. The combined solution is then purged with nitrogen flow for 1 hr, and then reduced by hydrogen flow for 20 minutes. The resulting solution constitutes the precursor solution. The selected zeolitic substrate, such as TS-1 in a powder form, is mixed into the precursor solution. After the substrate becomes impregnated with the solution, the substrate is removed from the solution, for example by filtration, and dried overnight. After drying, the impregnated substrate is reduced in hydrogen at 250–350° C. temperature for 10–20 hours. The dual-functional catalyst for producing propylene oxide is now ready for use.

EXAMPLE 2

Process Description

The dual-functional catalyst is advantageously used in an integrated process for the one-step synthesis of propylene oxide product from hydrogen oxygen, and propylene feeds. However, as will be apparent to those skilled in the art, the invention is not limited to the synthesis of propylene oxide. Olefins in general and mixtures of olefins may be used for epoxidation by the process of the invent, including C2–C20 olefins, substituted or unsubstituted with groups such as halogen, hydroxy, carboxy and the like.

Figure 2:
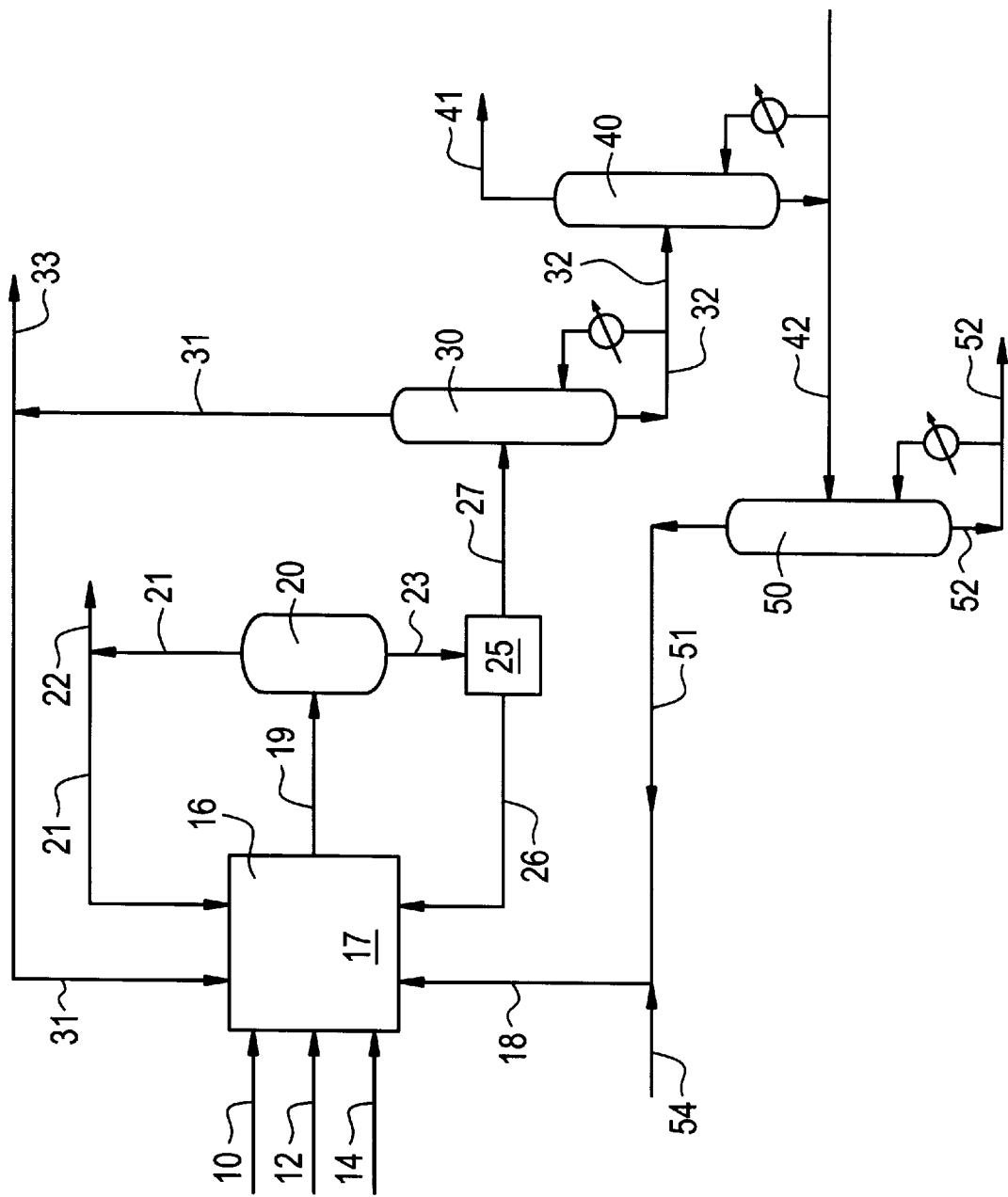
FIG. 2 is a schematic flowsheet of an integrated process for the production of propylene oxide using hydrogen, oxygen and propylene feeds and the dual-functional catalyst according to this invention.

A schematic flowsheet of an integrated process of the invention for propylene oxide production is depicted in FIG. 2. Hydrogen feed is provided at 10, and will preferably consist of a purified form of hydrogen, although it may also consist of a gaseous mixture containing hydrogen, such as synthesis gas, refinery off-gas, or the like. Oxygen feed is provided at 12, which may comprise purified oxygen, air, or enriched air. The optimal choice of the oxygen-containing feed will depend on a balance between the costs of oxygen purification against the costs of handling and removing inert nitrogen within the process, as can be determined using established design engineering and optimization practice. Fresh propylene feed is provided at 14, and may be in a liquid or gaseous state, but will preferably be in the liquid state. These hydrogen, oxygen and propylene feeds are introduced into reactor 16, along with a suitable solvent medium 18 for conducting the reaction. A variety of solvents may be used, including alcohols, ketones, aldehydes, ethers, esters, aromatic hydrocarbons, aliphatic hydrocarbons, and water, or mixtures thereof. The solvent will preferably be a mixture of alcohol and water, and more preferably a mixture of methanol and water.

The propylene oxide reactor 16 consists of a suitable reactor design which contains the dual functional catalyst 17, and contacts the catalyst with the reactants hydrogen, oxygen, and propylene. The raw product of the catalytic reaction is continuously withdrawn from the reactor 16 as stream 19.

The feeds to the reactor 16 include gaseous component (hydrogen, oxygen, propylene) which if combined inappropriately, would result in gaseous mixtures in the flammable or explosive regions. The lower flammability limits for hydrogen are 4.5 vol % in oxygen and 4.0 vol % in air. The lower explosive limits are 15.0 vol % in oxygen and 18.3 vol % in air. It is possible to operate reactor 16 with a gas composition that is within the flammable or explosive region, if suitable precautions are taken to eliminate ignition sources and provide for emergency shutdowns in the event of problems. However, it is preferred to maintain the gaseous composition within reactor 16 below the lower flammability limit, which provides for safe reactor operations.

The flammability and explosion characteristics of the gas in reactor 16 must also be considered with respect to the behavior of mixtures of propylene and oxygen or air. The lower and upper explosive limits for propylene in air, are 2 and 11 vol %, respectively. As discussed below, reactor 16 is preferably operated at a sufficiently high pressure such that the propylene is substantially in the liquid phase. This pressure must also be sufficiently high such that the gas phase propylene content is below the 2 vol % lower explosive limit. This limiting pressure may be determined by those skilled in the art based on published data for the vapor-liquid equilibrium of propylene-containing systems.

Reactor 16 may be one of several known reactor types. It may be a fixed bed reactor, in which the dual-functional catalyst 17 is held in an immobile bed and the gaseous and liquid reactants are passed through the catalyst bed. Liquid and gas flows may be passed through the bed in either upflow or downflow pattern, and may be fed in countercurrent or cocurrent flow configurations. Reactor 16 may alternately be of slurry, fluidized bed, transport bed, or any of a variety of related reactor types in which the catalyst is mobile and agitated within the liquid/gas mixture, either by the action of a mechanical agitator, or by the fluid motion of the liquids and gases. The mechanical design and operating conditions of the reactor are selected to ensure efficient contacting between the gas and liquid, and the catalyst solid.

Operating conditions in reactor 16 determine the performance of the process in terms of factors such as selectivity, yield, and the like. The operating temperature will be in the range 0–150° C., preferably 10–100° C. Higher temperatures in these ranges will favor higher rates of reaction, while lower temperatures will favor higher selectivity. Because the catalyst of this invention is dual functional, catalyzing two separate reactions in series, the choice of reactor temperature is especially critical. The reactor temperature must be optimally selected to balance the selectivity-activity requirements of two separate catalytic functions. In general, the best temperature for the performance of a separate noble metal catalyst in converting hydrogen and oxygen to in situ hydrogen peroxide is lower than the best temperature for the function of a separate zeolitic catalyst substrate for converting propylene and hydrogen peroxide to propylene oxide. The optimal reaction temperature for the dual functional catalyst of this invention represents a compromise between these competing requirements.

The optimal pressure for reactor 16 also depends on competing factors, and will be in the range 100–3000 psig, preferably 500–2000 psig. Generally, the pressure should be at least sufficiently high to maintain the propylene feed substantially in the liquid phase, thereby preventing explosive propylene-oxygen or propylene-air mixture from being present in the gas phase. This liquid phase also improves the contact between the catalyst and propylene feed, enhancing the rate and selectivity of the propylene oxide formation reaction. The reaction pressure must also be sufficiently high to force hydrogen to be dissolved in the liquid phase, as needed for the formation of in situ hydrogen peroxide at the noble metal active sites. But the reactor pressure should not be so high as to increase the capital and operating cost of the process equipment excessively. A balancing of these factors leads to the broad and preferred pressure ranges cited above.

The major liquid components present in reactor 16 are solvent, water, and propylene. The solvent is preferably an alcohol and more preferably methanol. Methanol and water are fully miscible, but propylene is only partially miscible in a methanol-water mixture. The solubility of propylene in methanol-water mixture will vary with the methanol-to-water ratio. Therefore, the liquid phase in reactor 16 may be a single liquid phase, or may consist of two phases. In the case of two phases, water will be primarily present in the aqueous phase, propylene in the organic phase, and methanol will tend to be distributed between the phases. While the two-phase case may be selected, it is preferable to operate the reactor in a region with a single liquid phase. Even with a gas-liquid-solid reaction system with a single liquid phase, efficient phase contacting in the three-phase system is a significant issue; and adding a fourth phase complicates matters further. Also, the dual functional catalyst must be in contact with all of the components to ensure that both catalyst function efficiently. The noble metal catalysts will operate most effectively in the methanol-water solution, and the in situ peroxide intermediate has a greater affinity for methanol-water than for propylene. The zeolitic epoxidation catalyst will function best if the propylene can easily reach the catalyst surface. Therefore, the dual functional catalyst will operate most efficiently if all liquid components are present in a single phase.

After exiting reactor 16, the reactor effluent stream 19 is subjected to a series of operation steps to recover various components for re-use, purification, or disposal. The precise details of this separation scheme or steps may vary in ways known to those skilled in the art. For example, the sequence of distillations can in some cases be reversed or permuted, removing different materials in a different sequence. The process configuration in FIG. 2 represents one suitable configuration.

The reactor effluent stream 19 is first passed into separator 20, where gaseous components are removed. The pressure of effluent stream 19 may be reduced before entering separator 20, but it is preferable to maintain stream 19 at a pressure near that of reactor 16. In this way, the recovered gas components require minimal recompression to be recycled back to reactor 16. As needed, the recovered gas is recycled to reactor 16 via stream 21, and any excess gas is purged from the process as stream 22. The relative amounts of gas that are recycled or purged will depend on several factors, especially the choice of the oxygen-containing feed 12. If air is used as the oxygen-containing feed, then most of the gases will be purged through stream 22 to prevent excessive build-up of nitrogen in the system. If purified oxygen is used as the feedstock, then most of the gases will be recycled via stream 21 to avoid wasting unreacted oxygen and hydrogen. Another factor influencing the ratio of purge to recycle gas is the amount of other gaseous impurities entering with the feeds or formed in the reactor, which need to be purged through stream 22 to prevent their building up excessively. For example, use of an impure hydrogen feed such as synthesis gas or refinery off-gas will necessitate a higher ratio of gas purging at 22 compared to recycling.

The net liquid and solid components of the reactor 16 effluent 19 exit separator 20 via stream 23, and enter catalyst recovery unit 25, which is only needed whenever a mobile catalyst 17 is used, such as for slurry or fluidized bed reactor. With a fixed bed reactor, the catalyst 17 remains immobilized in reactor 16 and does not need to be recovered from the reactor effluent 19. If catalyst recovery unit 25 is needed, the catalyst is recovered and returned to reactor 16 via stream 26. If the performance of catalyst 17 degrades over time, as is likely, spent catalyst may be removed from stream 26, and replaced with fresh or regenerated catalyst. Catalyst recovery unit 25 may be a filter, centrifuge, cyclone, settler, or other suitable means of removing dispersed solid particles from a liquid. Depending on its type and design, the catalyst recovery unit 25 may be physically integral to separator 20, or to reactor 16. As this implies, catalyst recovery unit 25 may precede separator 20, rather than following it as shown in FIG. 2.

The liquid effluent, now substantially free of gas and solid, passes as stream 27 into propylene recovery tower 30, which is a distillation system designed to remove unreacted propylene from the reactor effluent. Unreacted propylene is returned to reactor 16 as recycle stream 31. While propylene recovery tower 30 is depicted in FIG. 2 as a single distillation tower, it may in fact consist of multiple towers arranged in series or parallel. For example, propylene recovery may be conducted in two towers in series, with the first tower removing a portion of the propylene at a relatively high pressure, and the second tower removing the remaining propylene at a lower pressure. A process scheme of this type can be advantageous, in that it avoids excessively high temperatures in the bottom sections of the distillation towers and excessively low temperatures in the top sections. High temperatures in the bottoms sections could cause excessive decomposition or destructive reaction of the desired propylene oxide product. Low temperatures in the top sections could require expensive refrigeration for the tower condensers, and could cause pluggage due to freezing of water. The precise design details for such a distillation tower system 30 can be determined using well-established principles by those skilled in the art.

Recycle propylene stream 31 is returned to the reactor 16. However, stream 31 may contain other components with similar boiling points to propylene, which if not removed could accumulate in the system. In this case, a portion of stream 31 may need to be purged from the system at 33, or stream 31 may need to be subjected to some additional separation step or steps. For example, stream 31 is likely to contain propane, commonly present as an impurity in the feedstock propylene 14. This propane can be removed from stream 31 by an additional optional distillation step, not shown in FIG. 2.

The bottoms stream 32 from the propylene recovery tower 30 is next passed to propylene oxide tower 40, which is a distillation step that removes the propylene oxide product as an overhead product at 41. The remaining liquid exits via bottoms stream 42, and contains solvent, water, and heavier by-products and impurities. The recovered propylene oxide stream 41 is a crude product, which will generally require further purification, normally by additional distillation steps, to reach commercial requirements for purity of propylene oxide. Such additional distillation steps for Stream 41 are not shown in FIG. 2, but may be selected and designed based on known prior art.

The bottoms stream 42 from the propylene oxide tower 40 is passed to the solvent recovery tower 50. This distillation tower 50 separates the solvent from the water and other by-products and impurities formed in the process. The solvent is preferably a mixture of methanol and water, but may consist of other solvents or solvent mixtures as enumerated above. In any event, the solvent or solvent mixture preferably has a lower boiling point than water, such that the solvent can be recovered as an overhead stream from tower 50. The recovered solvent is recycled to reactor 16 via stream 51 and 18. Make-up solvent is added at 54 as needed to compensate for any solvent that is lost in the process.

The bottoms stream 52 from solvent recovery tower 50 contain the net water of reaction formed as a by-product of the propylene oxide synthesis, and also contain various organic by-products. These minor by-products include glycols such as propylene glycol, glycol ethers of methanol and propylene glycol, dipropylene glycol and other oligomerized propylene glycols, and other trace heavy by-products of the process. Stream 52 may be disposed as is, or may be subjected to further processing. For example, one or more of the by-products in stream 52 may have sufficient value to justify recovery and purification for sale. Environmental constraints and regulations may also require that certain processing of stream 52 must be used to qualify the materials for disposal. This processing could include waste water treatment, incineration, or other known methods.

An especially salient achievement of the instant invention employing the described process and dual-functional catalyst is the capability of the process to produce high yields of olefin epoxides such as propylene oxide from propylene while operating the process below the flammability limit of hydrogen of 4.5 volume percent in oxygen. Under these conditions, the process of the invention produces yields of olefin epoxide of at least 10 mole percent while the yields of hydrogen peroxide are at least 10 mole percent. These yields are defined as follows:

> Percent epoxide yield based on olefin=(percent olefin conversion)×(percent epoxide selectivity based on olefin converted)
>
> Percent hydrogen peroxide yield based on hydrogen=(percent hydrogen converted)×(hydrogen peroxide selectivity based on hydrogen converted)

What is claimed is:

1. A porous, particulate dual-functional catalyst for the selective combined in-situ production of hydrogen peroxide from hydrogen and oxygen concurrent with the epoxidation of olefins, the dual-functional catalyst comprising:
   a catalytic substrate material comprising at least one olefin epoxidation catalyst; and
   nanometer-sized crystallites of at least one noble metal deposited on a portion of the surface of said substrate wherein at least the face of the deposited crystallites include an exposition of the 110 and/or 220 series of crystal planes.

2. The dual-functional catalyst of claim 1 wherein said olefins are selected from the group comprising C2–C20 olefins, substituted or unsubstituted.

3. The dual-functional catalyst of claim 1 wherein said olefins comprise propylene.

4. The dual-functional catalyst of claim 1 wherein said oxygen includes air and oxygen enriched air.

5. The porous dual-functional catalyst of claim 1 wherein said noble metal is selected from the group consisting of palladium, platinum, gold, iridium, osmium, rhodium, ruthenium or combinations thereof.

6. The porous dual-functional catalyst of claim 1 wherein said noble metal comprises mixtures of a major amount of palladium and a minor amount of platinum.

7. The dual-functional catalyst of claim 6 wherein said noble metal comprises 0.01 weight percent to 10 weight percent of the dual-functional catalyst.

8. The dual-functional catalyst of claim 7 wherein said noble metal comprises 0.1 to 5 weight percent of the dual-functional catalyst.

9. The dual-functional catalyst of claim 1 wherein said catalytic substrate contains at least one metal epoxidation catalyst.

10. The dual-functional catalyst of claim 9 wherein the epoxidation catalyst is selected from the group consisting of titanium-substituted silicalite, vanadium-substituted silicalite and titanium-based zeolites.

11. The dual-functional catalyst of claim 9 wherein said epoxidation catalyst comprises titanium silicalite.

12. The catalyst of claim 10 wherein said titanium-based zeolites contain one or more elements selected from the group consisting of tellurium, boron, germanium and niobium.

13. The porous particulate dual-functional catalyst of claim 1 wherein said nanometer-size noble metal crystallites are between 0.1 and 1000 nanometers.

14. The dual-functional catalyst of claim 1 wherein the total surface area of the substrate is between 10 square meters per gram to 2000 square meters per gram.

15. The dual-functional catalyst of claim 1 having a selectivity for the production of hydrogen peroxide of at least 80 percent at hydrogen conversion of at least 10 percent.

16. The catalyst of claim 15 wherein said selectivity of hydrogen peroxide comprises at least 90 percent at hydrogen conversion of at least 10 percent.

17. A method for preparing a porous particulate dual-function catalyst comprising nanometer-sized noble metal crystallites deposited on a particulate catalytic substrate material comprising at least one olefin epoxidation catalyst for the concurrent production of hydrogen peroxide and epoxidation of an olefins feedstream, the method comprising:
   preparing a dilute acid solution containing a noble metal salt including a palladium salt alone or in combination with a minor amount of one or more salts of platinum, gold, iridium, osmium, rhodium or ruthenium;
   mixing at least one water-soluble noble metal complexing and dispersing polymer into the dilute acid solution of noble metal salt and reducing the mixed solution wherein a reduced and dispersed noble metal-polymer complex is formed;
   adding the particulate catalytic substrate to the reduced solution wherein the substrate is impregnated with the noble metal portion of the reduced mixed solution;
   recovering and drying the impregnated substrate; and
   reducing the impregnated substrate with hydrogen to produce the dual-function catalyst having nanometer-sized noble metal crystals wherein at least the face of the deposited noble metal crystals include an exposition of the 110 and/or 220 series of crystal planes.

18. The method of claim 17 wherein the production of hydrogen peroxide and the epoxidation of the olefins feedstream are carried out in situ.

19. The method of claim 17 wherein said polymer comprises an ionic polymer.

20. The method of claim 17 wherein said dilute acid solution comprises dilute hydrochloric acid solution.

21. The method of claim 17 wherein said ionic polymer is selected from the group consisting of polyacrylates, polyacids, polyacrylic acid, polyvinylbenzoates, polyvinylsulfate, polyvinysulfonates, polybiphenyl carbonates, polyvinylbenzimidazoles and polypyridines.

22. The method of claim 17 wherein said polymer comprises polyacrylates having a molecular weight between 300 and 8000.

23. The method of claim 22 wherein said molecular weight comprises between 600 and 6000.

24. The method of claim 17 wherein the ionic polymer is added to the dilute acid solution of noble metal salt in a molar ratio of about 1 of noble metal salt to polymer.

25. The method of claim 17 wherein the ionic polymer is added to the dilute solution of noble metal salt in a molar ratio in the range of from 0.2 to 2.

26. The method of claim 17 wherein the mixed solution is reduced in contact with hydrogen.

27. The method of claim 17 wherein the particulate catalytic substrate comprises a zeolitic catalyst substrate.

28. The method of claim 17 wherein the substrate includes titanium-substituted silicalites, vanadium-substituted silicalites and titanium-based zeolites alone or in combination with one or more of tellurium, boron, germanium and niobium having a surface area between 10 and 2000 square meters per gram.

29. The method of claim 17 wherein the impregnated substrate is recovered by filtration and dried at a temperature between 100 and 500 degrees centigrade.

30. The method of claim 17 wherein the dual-functional catalyst composition after reduction with hydrogen contains a noble metal loading of between 0.01 and 10 weight percent.

31. The method of claim 30 wherein the noble metal loading comprises between 0.1 and 5 weight percent.

32. A method for the epoxidation of olefins simultaneously with the selective generation of hydrogen peroxide, comprising concurrently contacting feedstreams comprising hydrogen, oxygen and olefins in a solvent in a reactor vessel containing the particulate dual-functional catalyst according to claim 1 under reaction conditions sufficient to generate hydrogen peroxide in situ from the hydrogen and oxygen feedstreams while epoxidizing the olefin feedsteam with the in situ generated hydrogen peroxide, wherein a reactor effluent stream is produced containing unreacted gaseous components, particulate catalyst, unconverted liquid olefins, olefin epoxides, solvent and water; and separating the reactor effluent stream to recover the olefin epoxide product and recover the particulate catalyst, unreacted olefin, unreacted hydrogen, unreacted oxygen and solvent.

33. The method of claim 32 wherein the yield of olefin epoxide from olefin is at least 10 mole percent and the yield of hydrogen peroxide from hydrogen is at least 10 mole percent when the method is carried out at hydrogen feed concentrations below the lower flammability limit of hydrogen in air, enriched air or oxygen.

34. The method of claim 32 wherein said olefin feedstream comprises propylene and said olefin epoxide comprises propylene epoxide.

35. The method of claim 32 wherein said reaction conditions comprise a reactor vessel temperature of 0 to 150 degrees centigrade and a pressure of 100 to 3000 psig.

36. The method of claim 35 wherein said reaction conditions comprise a reactor vessel temperature of 10 to 100 degrees centigrade and a pressure of 500 to 2000 psig.

37. The method of claim 32 wherein the epoxidation of olefins simultaneously with the selective generation of hydrogen peroxide is carried out in situ.

* * * * *